United States Patent [19]

Weinstein et al.

[11] Patent Number: 4,832,019
[45] Date of Patent: May 23, 1989

[54] ENDOTRACHEAL TUBE HOLDER

[76] Inventors: Burton Weinstein, 4 Windward La.; Peter Kyriakos, 89 Winter St., both of City Island, N.Y. 10464

[21] Appl. No.: 168,867

[22] Filed: Mar. 16, 1988

[51] Int. Cl.⁴ .......................... A62B 9/04; A61M 16/04
[52] U.S. Cl. ...................... 128/207.17; 128/DIG. 26; 128/912
[58] Field of Search ...................... 128/200.26, 200.28, 128/202.27, 207.14, 204.11, 207.17, 911, 912, DIG. 15, DIG. 26, 201.26, 206.27; 269/287; 24/70 J, 71 J

[56] References Cited

U.S. PATENT DOCUMENTS 3,602,227  8/1971  Andrew .......................... 128/207.17
3,976,080  8/1976  Bornhorst et al. .......... 128/DIG. 26
4,331,144  5/1982  Wapner ...................... 128/DIG. 26
4,351,331  9/1982  Gereg .......................... 128/DIG. 26

Primary Examiner—Edgar S. Burr
Assistant Examiner—Kimberly L. Asher
Attorney, Agent, or Firm—Darby & Darby

[57] ABSTRACT

An endotracheal tube holder having a locking piece and a center piece which are assembled so that one piece is movable relative to the other. Each piece has a part of a gripping jaw for the tube which is to be inserted in the patient's mouth and a locking arrangement which holds the two pieces in a fixed relationship with the gripping jaws aligned and holding the tube. The tube holder also has openings to provide access to the patient's mouth. The tube holder also has an integral bite block. Further, an integral taping projection is provided as well.

15 Claims, 2 Drawing Sheets

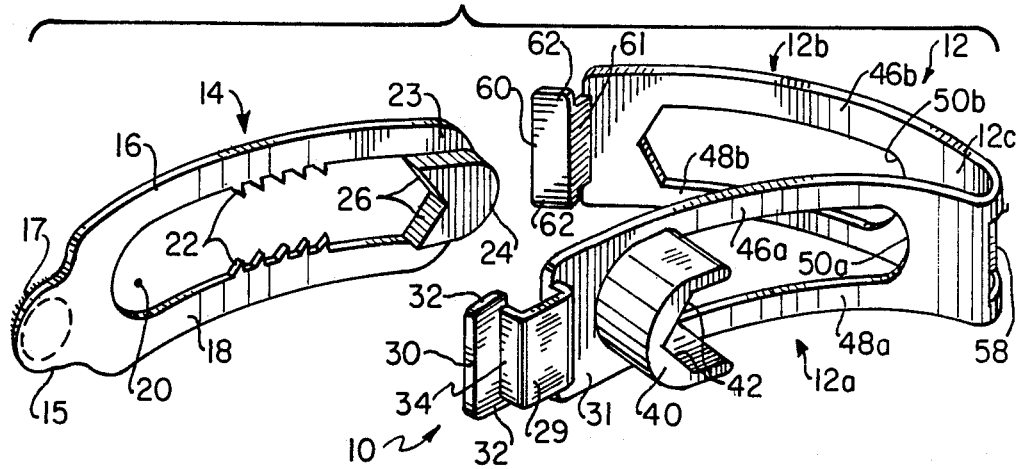

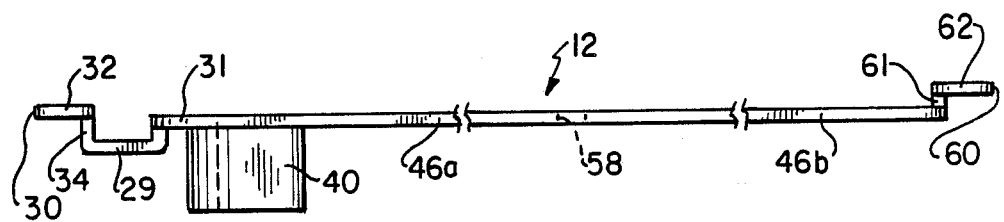
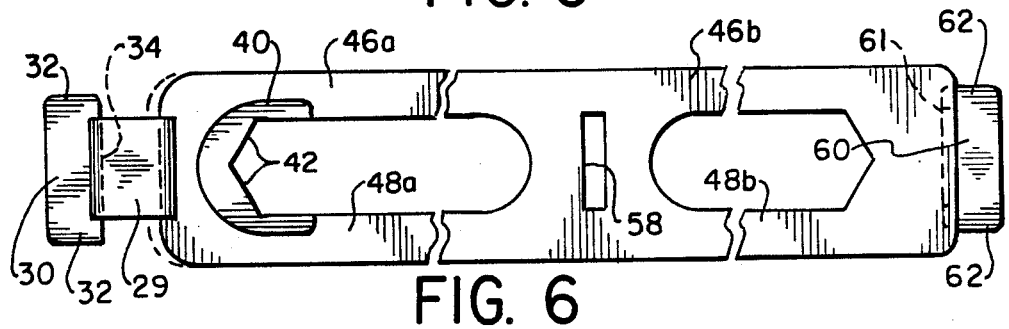
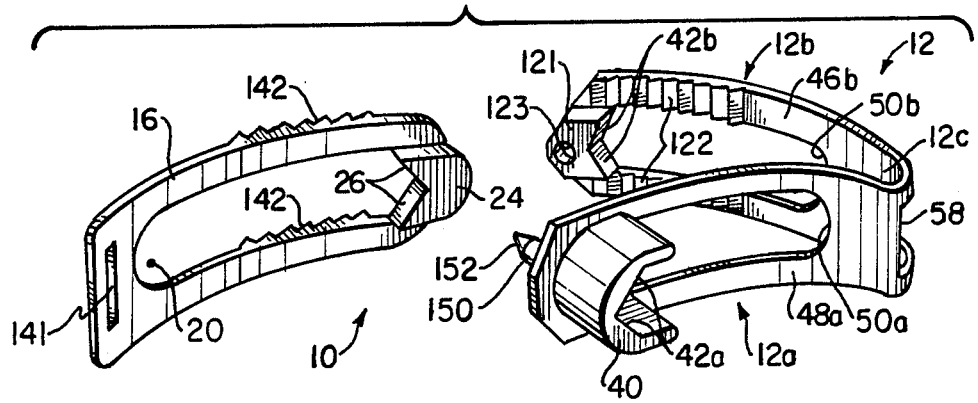
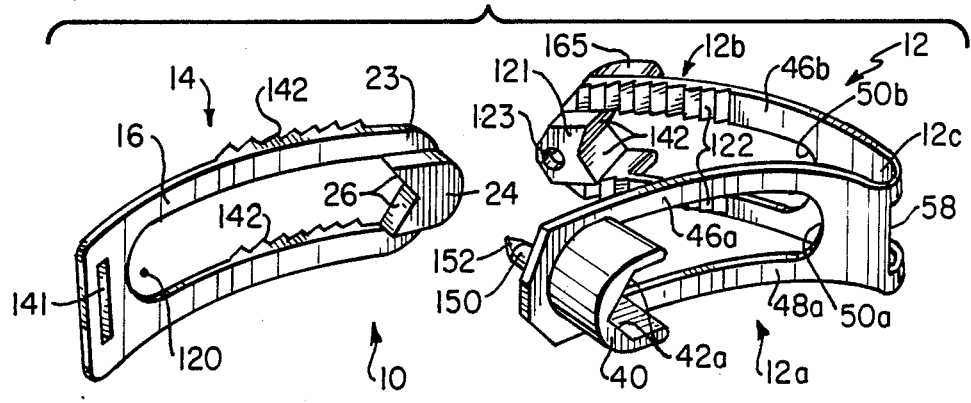

ENDOTRACHEAL TUBE HOLDER

BACKGROUND OF THE INVENTION

The present invention relates to an endotracheal tube holder. Such tube holders are known, for example, in the U.S. Pat. Nos. 4,325,515 to Shaffer et al, 4,520,813 to Young and 4,223,671 to Muto. Such devices are used, for example, in emergency medical service events as well as routine hospital and operating room requirements where a tube must be inserted directly through the mouth of a patient. The tube is inserted into the patient's mouth and trachea and the tube holder is then placed around the tube and over the patient's mouth and the integral bite block is inserted between the teeth.

The devices of the prior art have, in general, been somewhat complicated and do not readily adjust to accomodate a variety of different tube sizes. In addition, they also do not provide an arrangement for easily locking the tube securely nor give easy access to the patient's mouth while the tube is held by the holder and is in the patient's mouth. In addition, all of these devices have a cumbersome attachment system.

BRIEF SUMMARY OF THE PRESENT INVENTION

The present invention relates to an endotracheal tube holder formed of two or more pieces one of which is slidable relative to the other. In a preferred embodiment, the holder has a gripping arrangement, with a spiked or ridged surface, for holding the tube securely therein aligned in a position generally transverse to the holder as the pieces of the holder are adjusted to accommodate the size of the tube. A locking arrangement, of a ratchet type in the preferred embodiment, operates to securely hold the tube. In addition, the two pieces are formed with openings along their lengths so that when the holder is placed over the face of the patient, the openings are aligned with the mouth to provide access.

OBJECTS OF THE INVENTION

It is therefore an object of the present invention to provide an endotracheal tube holder which can accommodate a number of different sizes of supply tubes and lock the tube used firmly in position.

An additional object is to provide an endotracheal tube holder having openings therein which at all times provide access to the mouth of the patient.

A further object is to provide an endotracheal tube holder formed from two or more pieces of plastic material which readily conforms closely to the contours of the face.

An additional object is to provide an endotracheal tube holder which can easily be secured to the patient's head, provide access to the patient's mouth and can accommodate and securely hold a number of different size tubes.

Another object is to provide an endotracheal tube holder with a positive locking arrangement for holding the tube inserted into the patient's mouth.

An additional object is to provide a device for holding other orally routed tubes as well.

A further object is to provide an endotracheal tube holder with an integral bite block with a ridged surface to interact with the teeth to help hold it in position. Further, the bite block may be provided with a soft outer surface to accept the teeth or gums comfortably.

A further object is to provide an endotracheal tube holder with an integral protuberance extending outwardly and axially with the tube for use in optional taping of the endotracheal tube to the endotracheal tube holder.

BRIEF DESCRIPTON OF THE DRAWINGS

Other objects and advantages of the present invention will become more apparent upon reference to the following specification and annexed drawings in which:

FIG. 1 is a exploded perspective view of one embodiment of the holder;

FIG. 2 is a elevational view of the holder of FIG. 1 in assembled condition;

FIG. 3 is an plan view of the holder of FIG. 1 in on assembled condition;

FIG. 4 is a plan view of the locking and bite block end of one of the pieces of the holder of FIG. 1;

FIG. 5 is an elevational view of the other piece of the holder of FIG. 1;

FIG. 6 is a exploded, perspective view of a second embodiment of the invention; and FIG. 7 is an exploded perspective view of a third embodiment.

DETAILED DESCRIPTION OF THE INVENTION

Referring to the FIGS. 1-5 of the drawings, the tube holder 10 is formed of two pieces which are hereinafter referred to as the center piece 12 and the locking piece 14. The locking piece 14 it is of one piece construction, preferably molded from a suitable medically acceptable plastic material, e.g. polyethylene, which has reasonable flexibility and strength. In FIG. 1, the inside face of the locking piece is shown, i.e., the face which is to engage and ride over the center piece 12. Locking piece 14 has a tab 15 at one end thereof from which extends upper and lower frame rails 16 and 18 defining a generally elongated rectangular opening 20 therebetween. The opening 20 is, for example, wide enough to permit the mouth of the patient to be exposed therethrough, preferably for example, about one inch to three inches long and five eighth's of an inch to one inch between the rails 16, 18, but not limited to these particular dimensions.

A plurality of serrated ratchet teeth 22 are formed over a part of the inner edge of each of the two rails 16 and 18. The ratchet teeth 22 can occupy about one-third to one-half of the length of the rails 16, 18, starting from about one-third of the opening 20 closest to the tube 72. The number and exact location of the ratchet teeth are selected to cooperate with the center piece 12 as described below.

The end 23 of the locking piece 14 preferably has a raised shoulder 24 on its outer surface for use as part of the vise grip used to hold the tube. The inner face of the raised shoulder 24 is formed with two substantially straight edges 26 forming a V. As described below, they aid in holding the tube in place.

The outer face of the tab 15 has a piece of Velcro type material 17, either of the hook or loop type, affixed thereto by any suitable arrangement, for example, heat sealing, adhesive, etc. As explained below, this is used to fasten a strap which secures the holder 10 around the head of the patient.

The center piece 12 is formed of an elongated piece of plastic of the same type as the locking piece 14. In FIGS. 1 and 2 the piece is shown in its semi-folded condition of use with two sections 12a and 12b. Section 12a is the inner section which rests against the face of the patient (See FIG. 1) and in FIGS. 4 and 5 in an elongated condition.

Section 12a has a pair of frame members 46a and 48a which define an opening 50a therebetween which is of the same height and about the same length as the opening 20 of the locking piece 14. Starting from one end 31, there is an inner locking tab 30 on the upper end of an outer vertically extending arm of a connector 29 from which extend a pair of ears 32. In the assembled condition of the holder, the ears 32 partially overlay the rails 16 and 18 of the locking piece 14. The outer most arm of the connector has a width which permits it to ride between the ratchet teeth 22 on the inner edges of the two rails 16 and 18 of locking piece 14. The space between the two vertical arms of the U-shaped connector forms a pocket for another locking tab at the other end of the center piece.

A bite block 40 extends inwardly from the inner face of section 12a. The bite block is to be inserted into the mouth of the patient between his teeth. The bite block is made of a material soft enough to fit comfortably between the patient's teeth, yet hard enough to protect the tube to be inserted. The outer surface of the bite block 40 is generally U-shaped. It can be ridged or grooved so that a better grip on the block can be made by the teeth of the patient. The inner walls 42 of the bite block are generally V-shaped with a vertical extension at the end of each arm of the V to form four flat surfaces. The exact shape of the walls 46 can be varied as desired. When the holder is in the sassembled condition, the walls 46 oppose the inner walls 26 of the shoulder 24 of the locking piece 12 to hold the tube.

The other end section 12b has an opening 50b between rails 46b and 48b. A solid piece 12c extends between the two openings 50a, 50b and there is an elongated vertical slot 58 in the center of this piece to accept a strap which is used to secure the holder around the head of the patient. The two sections 12a, 12b fold around the slot 58.

At the free end of section 12b there is an inner locking tab 60 connected by a neck 61 to section 12b. The neck 61 also fits within the locking piece 14 opening 20 and engages the ratchet teeth 22. The outer locking tab 60 has locking ears 62 which, with the holder in the assembled condition, overlay the frame rails 16, 18.

As seen in FIGS. 2 and 3, which is the tube holder in the assembled condition, the center piece 12 has the neck 34 of the inner locking tab 30 extending through the opening 20 between the two frames 16, 18 of the locking piece 14 extending through the inner face and the ears 32 overlying the outer face of frame pieces 16, 18. The center piece is folded approximately at the slot 58 by 180°. The ears 62 of the outer locking tab 60 at the other end of the center piece 14 are inserted through the opening 20 of the locking piece 12 into the pocket of the connector 29 to lie on the inner face of the locking piece. This assembles and locks the two pieces 12 and 14 together.

With the two pieces 12, 14 assembled, there is now an opening 70 between the walls 26 of the shoulder 24 of the locking piece 14 and the walls 42 of the bite block. A tube 72 which is to be inserted into the patient's mouth fits in this opening.

To adjust the holder to accommodate different size tubes it is only necessary for the technician who applies the holder to the patient to take hold of the outer ends of parts 12 and 14 and pull them apart. The neck 34 of the locking tab 30 engages the ratchet teeth 22 on the frame pieces 16, 18 of the locking piece. As this movement takes place, the opening 70 for the tube between the walls 26 of the locking piece shoulder 24 and of the bite block 42 decrease in size. There is a positive locking action between the neck 34 and the ratchet teeth 22 at the final position selected. The final position selected is usually one in which the tube 72 is firmly held in the space 70 between the walls 26 and 42. The material of the pieces 12 and 14 are soft enough so they will not deform the wall of the tube 72 and thereby restrict the flow of the gas on fluid to be supplied to the patient.

A strap 78 has an end 79 which is inserted into the elongated slot 58 of the center piece 14. This can be accomplished by having ears on the end of the strap 78, by attaching it by heat sealing, adhesive, etc. Strap 78 preferably is of an elastic material. The other end of the strap 78 has a piece of Velcro material 80 of the type complementary to the piece 17 on the tab 15 of the locking piece 12.

In the use of the holder, the strap 78 is first placed around the head of the patient and secured by fastening the two pieces of Velcro material 17, 80 together. The bite block 40 is placed between the patient's teeth. The assembled holder is supplied in a position with the opposing tube gripping surfaces 26 and 42 spaced sufficiently wide enough apart to accept the largest size tube which is already inserted into the mouth of the patient. After the tube is positioned into the space 70, the technician pulls outer piece 14 away from the center piece 12 to firmly grasp the tube in a vise-like grip. This movement takes place with the neck 34 riding over the ratchet teeth 22.

Access is provided to the patient's mouth through the overlying aligned opening 20 and 50a, 50b.

It is often necessary to position the tube 70 to one side or the other of the patient's mouth. This can be easily accomplished merely by grasping the assembled holder and moving it over the mouth of the patient to the desired position.

FIG. 6 shows another embodiment of the invention in which the same reference numerals are used where applicable. Here, the locking piece 14 has a slot 141 on one end to accept an end of the head strap (not shown). Instead of having the ratchet teeth on the inner edges of the rails 16, 18 here teeth 142 are formed on the outer face of the center piece 14 rails 16–18 (looking from the head of the patient) and the inner face of each of the rails 46B, 48B, on center piece 12.

The center piece 12 has a reinforced shoulder 121 on the inner face of the free end of the section 12b. The shoulder 121 has a through hole 123 to the outer face which has a recess (not shown). A locking pin 150 having a conical locking head 152 is formed on the inner face of the free end of center section 12a. The locking pin 150 is to extend into the locking hole 123 at the end of the other section 12b.

Ratchet teeth 122 are formed on the inner surface of each of the rails 46b, 48b which are to engage with the teeth 142 on the two rails of the locking piece. The ratchet teeth 122, 142 are preferably formed to permit only one way motion of the shoulder 24 on the locking piece toward the bite block 40 of the center piece to close the opening 70 betwen them so that the tube can be securely held. The ratchet faces may be pulled apart sufficiently to permit reverse motion if necessary for readjustment.

To assemble the device, locking piece 14 is laid between the two sections 12a, 12b of the center piece. The gripping shoulder 24 of the locking piece extends through the space between the two rails 46a, 46b of section 12a. The two sections 12a, 12b are folded and locked by inserting the pin 150 into the hole 123 and the undersurface of the conical head 152 locks on the shelf of the recess on the hole 123 at outer face of section 12b. Again, the device is preferably packaged and shipped away from the bite block tube gripping surfaces 42 by a distance corresponding to the maximum tube diameter.

The tube holder is placed over the patient's mouth by passing the elastic or other type of strap (not shown) around the patient's head. The locking piece 14 is pulled to close the opening 70. A firm gripping action is achieved due to the one way action of the mating ratchet teeth 122, 124. As before, the entire tube holder 10 can be moved relative to the mouth of the patient and access provided through the rails.

FIG. 7 shows a modification which can be used with any of the embodiments heretofore described. Here, a taping block 165 is formed on the end of the outer surface of section 12b of the center piece. The taping block generally corresponds in shape to the bite block 40 on the inner face of section 12a, so that the tube can pass through the frame opening to the gripping jaws 24, 121 and the bite block 40. Once the tube is in place, a strip of adhesive, or other tape can be wrapped around the tube and taped to the taping block 165. Some medical technicians desire this for additional security although the gripping jaws normally provides a firm enough grip for the tube. There is still access to the mouth of the patient through the windows in the sections of the center piece.

The endotracheal tube holder of the invention is simple to manufacture, being preferably made of the molded pieces and is easy to assemble. A positive gripping action is provided to securely hold the tube inserted into the patient's mouth.

As can be seen, a novel and economic endotracheal tube holder has been disclosed. The holder is economical to make and assemble. It has considerable advantage in the manner in which a firm locking of the tube can be achieved and at the same time that a full access through the holder's openings to the mouth of the patient is also made available.

What is claimed:

1. An endotracheal tube holder comprising:
   an elongated center piece for placement over the mouth of a patient;
   said center piece intregally formed with a first part of a tube gripping jaw,
   an elongated locking piece integrally formed with a second part of said tube gripping jaw;
   said center piece and said locking piece being flexible along each of their respective lengths to permit said pieces to conform to the shape of the face of the patient,
   means for holding said two pieces together while permitting a sliding relationship therebetween along a substantial part of the length of said pieces;
   and means for locking said two pieces from sliding with the two jaw parts in a position with the tube held therebetween.

2. An endotracheal tube holder as in claim 1 where each of said center and locking pieces has an elongated slot therein along a part of its length adjacent its jaw part which is aligned with the slot of the other piece when the two pieces are assembled to permit further access through said aligned slots to the patient's mouth.

3. An endotracheal tube holder as to claim 1 where said first part of said tube gripping jaw extends inwardly from the center piece so as to project into the mouth of the patient to form a bite block.

4. An endotracheal tube holder as in claim 1, wherein said means for locking said two pieces from sliding comprises ratchet teeth on one of said pieces and means on said other piece for engaging said ratchet teeth.

5. An endotracheal tube holder as in claim 4 wherein said ratchet teeth and said engaging means permit only one way sliding motion in a direction to bring said gripping jaw parts closer together yet permitting separation of ratchet surfaces if necessary for readjustment.

6. An endotracheal tube holder as in claim 4 wherein said ratchet teeth are formed on one face of said center piece and said engaging means comprises ratchet teeth formed on a face of said locking piece opposing said one face.

7. An endotracheal tube holder as in claim 3 further comprising an outwardly extending projection on the outer face of said center section to form a taping block for use in optional taping of the tube to the holder.

8. An endotracheal tube holder as in claim 2 wherein said center piece comprises an elongated member which is folded to form two sections each having a slot therein, said locking piece sliding within the folded sections of said center piece, said means for holding said two pieces together comprising mating means on the opposing free ends of the two folded sections of said center piece.

9. An endotracheal tube holder as in claim 8 wherein said mating means comprises an opening in the free end of one section, and a locking piece on the free end of said other section which fits into said opening.

10. An endotracheal tube holder as in claim 9 wherein said mating means comprises a latching channel formed on the free end of one of said sections of said center piece, and a latching tab on the free end of the other center piece section.

11. An endotracheal tube holder as in claim 1 in which the gripping surface of at least one of said gripping jaws which is to engage the tube is provided with a spiked or ridged surface.

12. An endotracheal tube holder as in claim 3 wherein said bite block is of flexible material.

13. An endotracheal tube holder as in claim 1 wherein the interior surface of at least one of said gripping jaws which is to engage the tube has a plurality of flat walls.

14. An endotracheal tube holder as in claim 1 further comprising a strap to fasten the holder onto the head of the patient, said strap having one end attached to the end of one of said pieces, remote from the jaw part thereon, and mating fastening means on the other end of said strap and the end of the other piece remote from the jaw part thereon.

15. An endotracheal tube holder as in claim 1 further comprising a strap to fasten the holder onto the head of the patient, such strap having an end attached to the end of each of said pieces remote from the jaw part.

* * * * *